(12) United States Patent
Cook et al.

(10) Patent No.: US 8,016,880 B2
(45) Date of Patent: Sep. 13, 2011

(54) STENT HAVING SPIRAL CHANNEL FOR DRUG DELIVERY

(75) Inventors: Brian Cook, Windsor, CA (US); Mark Dolan, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 597 days.

(21) Appl. No.: 11/941,591

(22) Filed: Nov. 16, 2007

(65) Prior Publication Data

US 2009/0132031 A1 May 21, 2009

(51) Int. Cl.
*A61F 2/06* (2006.01)
(52) U.S. Cl. .................. 623/1.42; 623/1.22
(58) Field of Classification Search .......... 623/1.42, 623/1.22
See application file for complete search history.

(56) References Cited

U.S. PATENT DOCUMENTS

| | | | |
|---|---|---|---|
| 4,886,062 A | 12/1989 | Wiktor | |
| 4,969,458 A | 11/1990 | Wiktor | |
| 5,133,732 A | 7/1992 | Wiktor | |
| 5,653,727 A | 8/1997 | Wiktor | |
| 5,782,903 A | 7/1998 | Wiktor | |
| 5,891,108 A | 4/1999 | Leone et al. | |
| 6,071,305 A * | 6/2000 | Brown et al. | 623/1.43 |
| 6,113,621 A | 9/2000 | Wiktor | |
| 6,258,121 B1 | 7/2001 | Yang et al. | |
| 6,273,913 B1 | 8/2001 | Wright et al. | |
| 6,358,556 B1 | 3/2002 | Ding et al. | |
| 6,364,856 B1 | 4/2002 | Ding et al. | |
| 6,623,519 B2 | 9/2003 | Edwin et al. | |
| 6,656,219 B1 | 12/2003 | Wiktor | |
| 6,663,661 B2 | 12/2003 | Boneau | |
| 6,709,451 B1 | 3/2004 | Noble et al. | |
| 6,923,828 B1 | 8/2005 | Wiktor | |
| 7,122,048 B2 | 10/2006 | DiMatteo et al. | |
| 2002/0151968 A1* | 10/2002 | Zilla et al. | 623/1.39 |
| 2004/0133270 A1* | 7/2004 | Grandt | 623/1.42 |
| 2005/0043783 A1* | 2/2005 | Amis et al. | 623/1.22 |
| 2005/0171593 A1* | 8/2005 | Whirley et al. | 623/1.13 |
| 2007/0154554 A1* | 7/2007 | Burgermeister et al. | 424/486 |

FOREIGN PATENT DOCUMENTS

| | | |
|---|---|---|
| WO | WO00/18327 | 4/2000 |
| WO | WO00/18331 | 4/2000 |
| WO | WO2004/004602 | 1/2004 |
| WO | WO2007/149184 | 12/2007 |

\* cited by examiner

*Primary Examiner* — David H Willse
*Assistant Examiner* — Tiffany Shipmon (57) ABSTRACT

A drug delivery stent is formed by a metallic or polymeric tubular strut which is shaped into a generally cylindrical configuration, the tubular strut having a central lumen for containing a therapeutic substance or drug therein. The tubular strut has a continuous channel extending from the inside surface of the strut to the outside surface of the strut positioned spirally about or in a corkscrew fashion around a circumference of the tubular strut for delivering the therapeutic substance or drug to a stenotic lesion. The spiral or corkscrew channel width may be varied along the length of the strut to control elution rate and/or flexibility of the stent. The pitch of the spiral or corkscrew channel may also be varied along the length of the strut to control flexibility of the stent. The stent may be carried on a balloon of a balloon catheter to a site of a stenotic lesion where the stent is implanted.

23 Claims, 5 Drawing Sheets

STENT HAVING SPIRAL CHANNEL FOR DRUG DELIVERY

FIELD OF THE INVENTION

The present invention relates generally to endoluminal prostheses, and more particularly to stents for delivering a drug or therapeutic substance to a body lumen.

BACKGROUND OF THE INVENTION

A wide range of medical treatments are known that utilize "endoluminal prostheses." As used herein, endoluminal prostheses are intended to mean medical devices that are adapted for temporary or permanent implantation within a body lumen, including both naturally occurring and artificially made lumens. Examples of lumens in which endoluminal prostheses may be implanted include, without limitation: arteries, such as those located within the coronary, mesentery, peripheral, or cerebral vasculature; veins; gastrointestinal tract; biliary tract; urethra; trachea; hepatic shunts; and fallopian tubes.

Various types of endoluminal prostheses are also known, each providing a structure for modifying the mechanics of the targeted luminal wall. For example, stent prostheses are known for implantation within body lumens for providing artificial radial support to the wall tissue, which forms the various lumens within the body, and often more specifically within the blood vessels of the body.

To provide radial support to a blood vessel, such as one that has been widened by a percutaneous transluminal coronary angioplasty, commonly referred to as "angioplasty," "PTA" or "PTCA", a stent is implanted in conjunction with the procedure. Effectively, the stent must overcome the natural tendency of the vessel walls of some patients to close back down. As such, the stent acts as a scaffolding to resist the vessels tendency to close back down. Under this procedure, the stent may be collapsed to an insertion diameter and inserted into a body lumen at a site remote from the diseased vessel. The stent may then be delivered to the desired treatment site within the affected lumen and deployed, by self-expansion or radial expansion, to its desired diameter for treatment.

In addition, it may be desired to deliver a therapeutic substance to the treatment site in order to reduce the incidence of restenosis. Thus various drug eluting stents are known that simultaneously deliver a therapeutic substance to the treatment site while providing artificial radial support to the wall tissue. Therapeutic substances that may be delivered include antiplatelet agents, anticoagulant agents, antimicrobial agents, and antimetabolic agents. Endoluminal devices including stents are sometimes coated on their outer surfaces with a substance such as a drug releasing agent, growth factor, or the like. Stents have also been developed having a hollow tubular structure with holes or ports cut through the sidewall to allow drug elution from a central lumen, such as the stents disclosed in U.S. Pat. No. 5,891,108 to Leone et al., which is incorporated by reference herein in its entirety. The hollow nature of the stent allows the central lumen to be loaded with a drug solution that is delivered via the ports or holes in the sidewall of the stent.

As will be described in greater detail below, the present invention provides a drug eluting stent for delivering a therapeutic substance or drug to a stenotic lesion. It is desirable to provide a flexible drug delivery device having a passageway for the drug to elute from the inside of the stent while minimizing the loss of mechanical integrity.

BRIEF SUMMARY OF THE INVENTION

Embodiments of the present invention are directed to a drug eluting stent having a generally cylindrical configuration for placement within a body lumen. The stent comprises a tubular strut having a central lumen defined by an inner surface of the tubular strut, the tubular strut shaped into the generally cylindrical configuration of the stent. A channel is formed in the tubular strut in a spiraling fashion, the spiral channel having a depth that extends between the inner and outer surfaces of the tubular strut and a length that extends from substantially a proximal end to a distal end of the tubular strut. A therapeutic substance is disposed within the central lumen of the tubular strut for delivery to a body vessel via the spiral channel. The tubular strut may be shaped into a coil configuration, an undulating or zigzag ring configuration, or any generally cylindrical configuration to form the stent.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as periphery and coronary arteries, the invention may also be used in any other body passageways where it is deemed useful. Furthermore, there is no intention to be bound by any expressed or implied theory presented in the preceding technical field, background, brief summary or the following detailed description.

In accordance with embodiments of the present invention, a stent is formed from a hollow tubular strut that is shaped into a generally cylindrical configuration, the tubular strut includes a channel extending from the inside surface of the strut to the outside surface of the strut that is positioned spirally about or in a corkscrew fashion around a circumference of the tubular strut for delivering a therapeutic substance or drug to a stenotic lesion. The spiral or corkscrew channel provides a passageway for the drug to elute from the inside of the tubular strut to the target body lumen while minimizing the loss of mechanical integrity of the stent prostheses. The spiral or corkscrew channel provides for uniform distribution of the therapeutic substance or drug to the vessel's luminal and abluminal surfaces.

The spiral or corkscrew channel causes the tubular strut to be extremely flexible and thus eliminates kinking when the strut is formed into a stent having a generally cylindrical shape for delivery by a balloon of the balloon catheter. In order to further increase flexibility of the stent, the pitch of the spiral or corkscrew channel of the tubular strut may be varied along the length thereof. For example, the pitch of the spiral or corkscrew channel may be decreased at a particular location on the tubular strut in order to increase flexibility. This decreased pitch may be desirable at the crown or turns of the tubular strut when the tubular strut is formed into a stent having a generally cylindrical shape, such as a stent with a coil configuration or a stent with an undulating ring configuration.

The width of the channel may be selected to control the elution rate of the therapeutic substance or drug contained within the tubular strut. In addition, the width of the channel may be varied along the length of the tubular strut to further increase the flexibility of the stent. For example, the width of the spiral or corkscrew channel may be increased at a particular location on the tubular strut in order to increase flexibility. This increased width is desirable at the crown or turns of the tubular strut when the tubular strut is formed into a stent having a generally cylindrical shape, such as stent having a coil configuration or an undulating ring configuration. Further details and description of the embodiments of the present invention are provided below with reference to FIGS. 1-7A.

Figure 1:
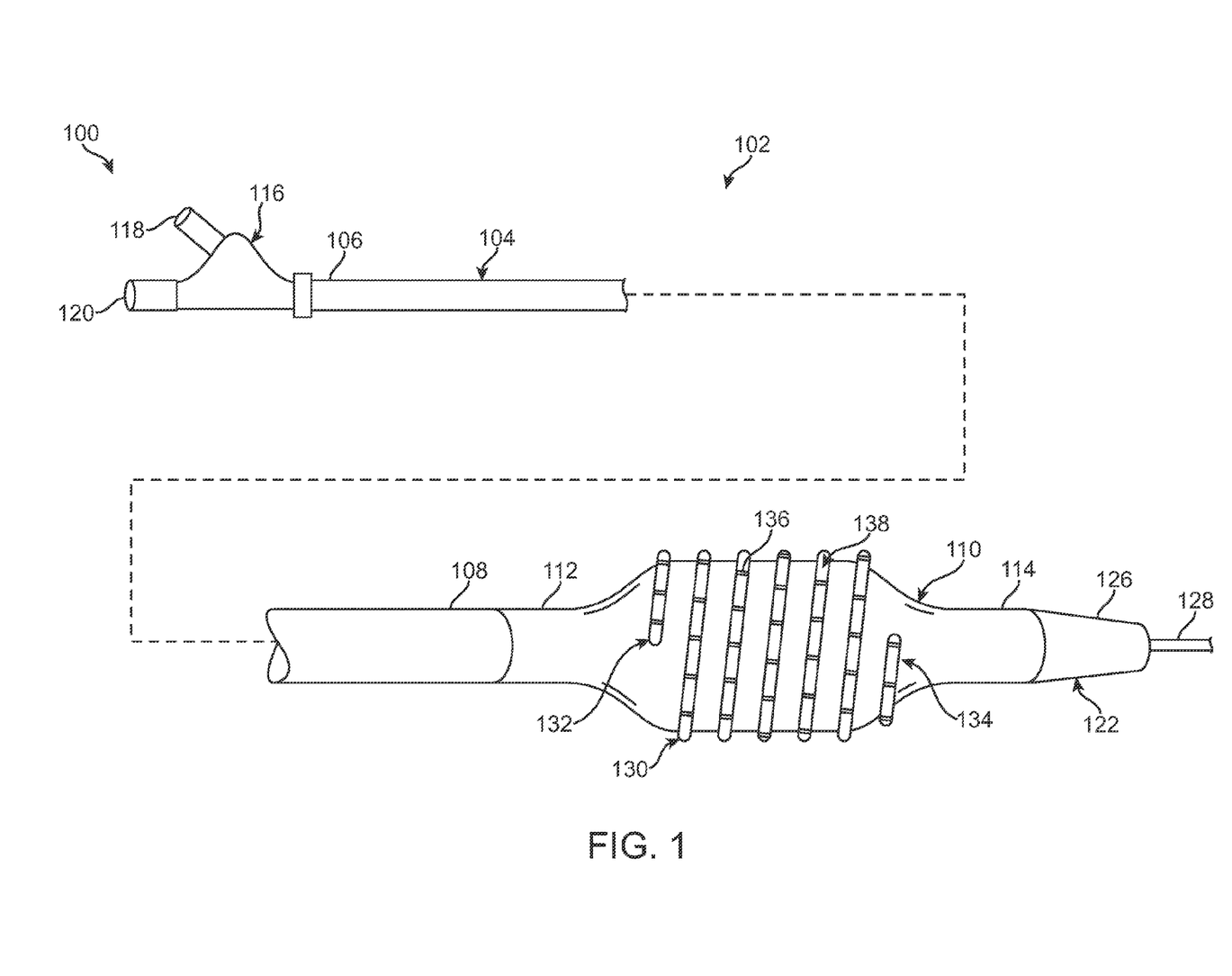
FIG. 1 is an illustration of a stent delivery system in accordance with an embodiment of the present invention.

FIG. 1 is an illustration of a stent delivery system 100 in accordance with an embodiment of the present invention. Stent delivery system 100 includes a catheter 102 having a proximal shaft 104, a guidewire shaft 122, and a balloon 110 having a proximal end 112 and a distal end 114. Proximal shaft 104 has a proximal end 106 attached to a hub 116 and a distal end 108 attached to the proximal end 112 of balloon 110. Guidewire shaft 122 extends between hub 116 and a distal tip 126 of catheter 102 through proximal shaft 104 and balloon 110. Hub 116 includes an inflation port 118 for coupling to a source of inflation fluid. Inflation port 118 fluidly communicates with balloon 110 via an inflation lumen (not shown) that extends through proximal shaft 104. In addition, hub 116 includes a guidewire port 120 that communicates with a guidewire lumen (not shown) of guidewire shaft 122 for receiving a guidewire 128 there through. As described herein, guidewire shaft 122 extends the entire length of catheter 102 in an over-the-wire configuration. However, as would be understood by one of ordinary skill in the art, guidewire shaft 122 may alternately extend only within the distal portion of catheter 102 in a rapid-exchange configuration. A stent 130 formed from a tubular strut 138 having a proximal end 132 and a distal end 134 is positioned over balloon 110. Stent 130 has a continuous channel 136 extending spirally about, or in a corkscrew fashion around, a circumference of tubular strut 138 for delivering a therapeutic substance or drug.

Deployment of balloon expandable stent 130 is accomplished by threading catheter 102 through the vascular system of the patient until stent 130 is located within a stenosis at a predetermined treatment site. Once positioned, balloon 110 of catheter 102 is inflated to expand stent 130 against the vascular wall to maintain the opening. Stent deployment can be performed following treatments such as angioplasty, or during initial balloon dilation of the treatment site, which is referred to as primary stenting.

Figure 2:
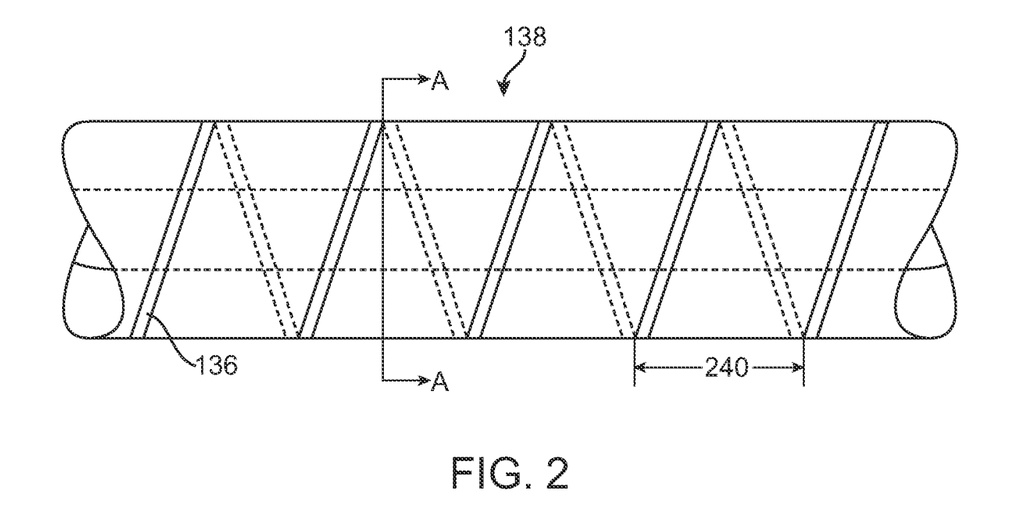
FIG. 2 is an enlarged view of a portion of a tubular strut for use in a stent in accordance with an embodiment of the present invention.
Figure 3:
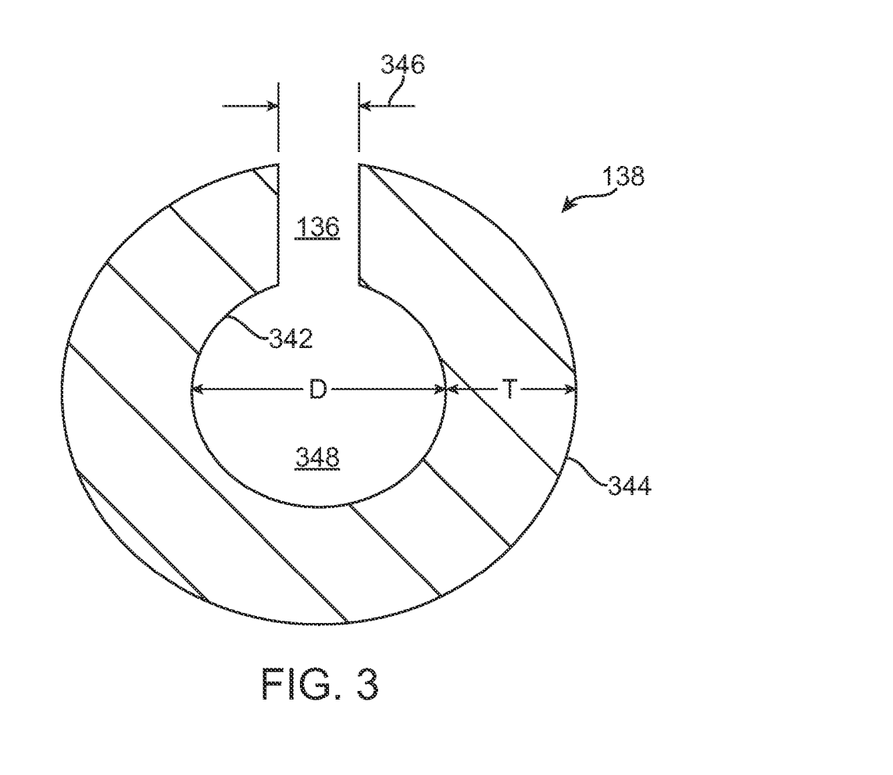
FIG. 3 is a cross-sectional view of the tubular strut of FIG. 2 taken along line A-A.

FIG. 2 is an enlarged view of a portion of tubular strut 138 prior to being formed into stent 130. FIG. 3 is a cross-sectional view of tubular strut 138 taken along line A-A of FIG. 2. Although tubular strut 138 is illustrated as having a circular cross-section, any cross-section may be suitable as long as the strut includes a lumen there through. Tubular strut 138 includes a central lumen or fluid passageway 348 for holding a therapeutic substance or drug therein. Channel 136 has a depth that extends from an inside surface 342 of tubular strut 138 to an outside surface 344 of tubular strut 138 so that the therapeutic substance or drug located in central lumen 348 may be delivered to a body lumen. Thus once tubular strut 138 is formed into stent 130; channel 136 extends in a spiral fashion about tubular strut 138 along a length of stent 130 to provide a passageway for the drug or therapeutic substance to elute from stent 130, while minimizing the loss of mechanical integrity of the stent prosthesis. In addition, spiral or corkscrew channel 136 is continuous around a circumference of tubular strut 138 and thus provides uniform distribution of the therapeutic substance to the vessel's luminal and abluminal surfaces.

A volume of central lumen or fluid passageway 348 controls the amount of therapeutic substance or drug that may be contained for delivery within stent 130. In an embodiment, fluid passageway 348 may extend from proximal end 132 to distal end 134 of tubular strut 138 and have a diameter "D" of approximately 0.001 inches to 0.004 inches. In another embodiment, fluid passageway 348 may extend for less than the full length of tubular strut 138. To increase radial strength of stent 130, a smaller diameter "D" will allow for a greater wall thickness "T" to maximize the material of stent 130. However, a larger diameter "D" may allow for a larger quantity of therapeutic substance or drug to be delivered to the body lumen.

Spiral or corkscrew channel 136 includes a width 346. In an embodiment, width 346 may be approximately 0.0005 inches and may be selected in order to control the elution rate of the therapeutic substance or drug. In another embodiment, width 346 may range from zero, which would occur if the edges of channel 136 touched, to 0.002 inches. In another embodiment, width 346 may be tapered along the length of tubular strut 138 and may range from zero, which would occur if the edges of channel 136 touched, to 0.002 inches. In general, a narrow width 346 of channel 136 will provide slower elution of the therapeutic substance or drug. Further, narrow widths 346 of channel 136 will maximize the remaining material of stent 130, thus increasing radial strength and minimizing loss of mechanical integrity of the stent prosthesis. In general, wider widths 346 of channel 136 will minimize the remaining material of stent 130 and thus may be desirable if stent 130 is formed of a biodegradable material. When spiral or corkscrew channel 136 is formed by a laser, width 346 of channel 136 may be selected by controlling the laser focus as desired.

Figure 4:
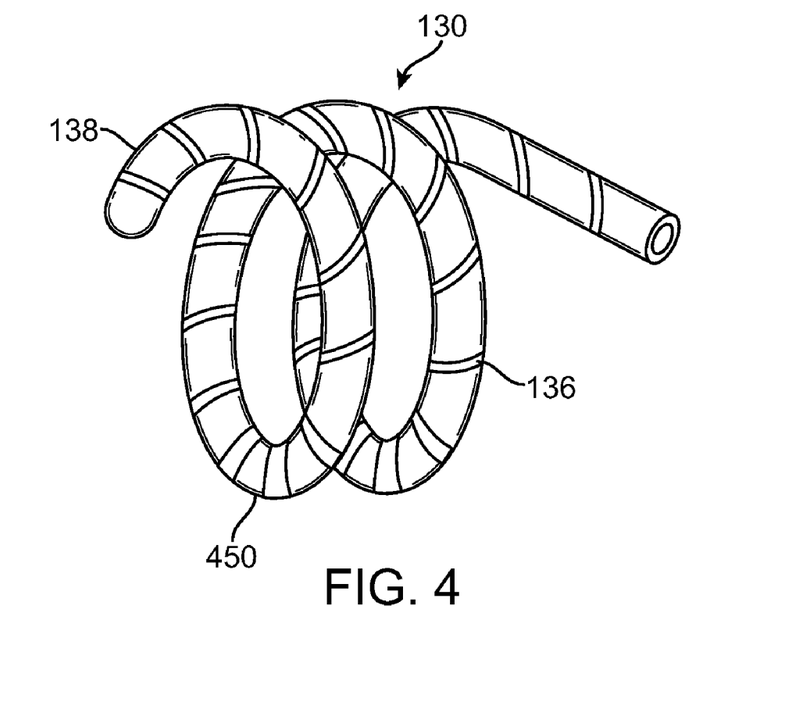
FIG. 4 is a perspective view of a stent incorporating the tubular strut of FIG. 2 in accordance with an embodiment of the present invention.

Spiral or corkscrew channel 136 provides flexibility to tubular strut 138 and eliminates kinking of tubular strut 138 when it is shaped into a stent having a generally cylindrical configuration for positioning around balloon 110 of catheter 102. The turns of spiral or corkscrew channel 136 have a pitch 240, which is the distance between two corresponding points on adjacent turns of channel 136. In order to further increase flexibility of stent 130, pitch 240 of spiral or corkscrew channel 136 may be varied along the length of tubular strut 138. For example, pitch 240 of spiral or corkscrew channel 136 may be decreased at a particular location on stent 130 in order to increase flexibility of stent 130 at the particular location. As illustrated in FIG. 4, a decrease in pitch 240 may be desirable at a turn or crown 450 of stent 130 when tubular strut 138 is bent into a coil configuration thereby forming stent 130. A decrease in pitch 240 of channel 136 may be desirable at any location on stent 130 where additional flexibility is desirable.

In addition, width 346 of spiral or corkscrew channel 136 may be varied along the length of tubular strut 138 to further increase the flexibility of stent 130. For example, width 346 of spiral or corkscrew channel 136 may be increased at a particular location on stent 130 in order to increase flexibility of stent 130 at the particular location. As illustrated on FIG. 4, this increased width 346 may be desirable at crown 450 of stent 130 when tubular strut 138 is bent into a coil configuration thereby forming stent 130. An increase in width 346 of channel 136 may be desirable at any location on stent 130 where additional flexibility is desirable. When spiral or corkscrew channel 136 is formed by a laser, width 346 of channel 136 may be varied along the length of tubular strut 138, as desired, by changing the laser focus.

Figure 5:
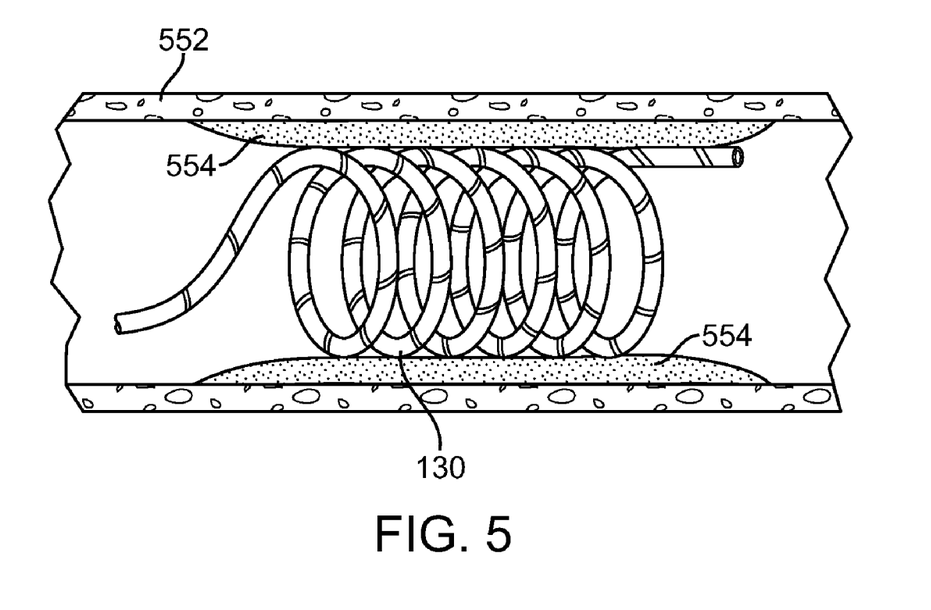
FIG. 5 is a side view of the stent of FIG. 4 deployed in a body lumen.

FIG. 5 is a side view of stent 130 deployed against the walls 552 of a body vessel for treating a stenotic lesion 554. In various embodiments of the present invention, the elutable therapeutic substance or drug contained in central lumen 348 of tubular strut 138 may be one or more substances useful for delivering to the body lumen. The drug delivered to the area of stenotic lesion 554 can be of the type that dissolves plaque material forming the stenosis or can be an anti-platelet formation drug, an anti-thrombotic drug, or an anti-proliferative drug. Such drugs can include TPA, heparin, urokinase, or sirolimus, for example. Of course stent 130 can be used for delivering any suitable medications to the walls and interior of a body vessel.

In various embodiments of the present invention, the elutable therapeutic substance or drug contained in central lumen 348 may comprise a biologically or pharmacologically active substance. In one embodiment, the elutable therapeutic substance or drug contained in central lumen 348 may be in crystalline form. In another embodiment, the biologically or pharmacologically active substance may be suspended in a polymer matrix or carrier to prevent premature elution of the active therapeutic substance from central lumen 348 until stent 130 has been implanted at the treatment site. Methods of making a polymer carrier or matrix for biologically or pharmacologically active ingredients are well known in the art. Biologically or pharmacologically active substances and carriers for these substances are listed in U.S. Pat. Nos. 6,364,856; 6,358,556; and 6,258,121; each of which is incorporated by reference herein in its entirety. These patent references disclose active substances, as well as polymer materials impregnated with the active substances for use as coatings on the outside of medical devices to provide controlled delivery of the active substances. These same polymer materials impregnated with active substances may be used within central lumen 348 of stent 130 of the present invention. In one embodiment, the polymer matrix or carrier is biodegradable or bioresorbable such that it is absorbed in the body. Polylactic acid (PLA), polyglycolic acid, polyethylene oxide (PEO), and polycaptrolactone are examples of biodegradable polymeric carriers.

The term "biologically or pharmacologically active substance" refers to any substance, whether synthetic or natural, that has a pharmacological, chemical, or biological effect on the body or a portion thereof. Suitable biologically or pharmacologically active materials that can be used in embodiments of the present invention include without limitation glucocorticoids (e.g. dexamethasone, betamethasone), antithrombotic agents such as heparin, cell growth inhibitors, hirudin, angiopeptin, aspirin, growth factors such as VEGF, antisense agents, anti-cancer agents, anti-proliferative agents, oligonucleotides, antibiotics, and, more generally, antiplatelet agents, anti-coagulant agents, antimitotic agents, antioxidants, antimetabolite agents, and anti-inflammatory agents may be used. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents may include drugs such as heparin, protamine, hirudin and tick anticoagulant protein. Anti-cancer agents may include drugs such as taxol and its analogs or derivatives. Taxol is also classified as a cell-growth inhibitor. Antioxidant agents may include probucol. Anti-proliferative agents may include drugs such as amlodipine, doxazosin, and sirolimus or other—limus family compounds. Antimitotic agents and antimetabolite agents may include drugs such as methotrexate, azathioprine, vincristine, vinblastine, 5-fluorouracil, adriamycin and mutamycin. Antibiotic agents can include penicillin, cefoxitin, oxacillin, tobramycin, and gentamicin. Suitable antioxidants include probucol. Also, genes or nucleic acids, or portions thereof may be used. Such genes or nucleic acids can first be packaged in liposomes or nanoparticles. Furthermore, collagen-synthesis inhibitors, such as tranilast, may be used.

In one embodiment, the elutable therapeutic substance or drug may be pre-loaded into stent 130 prior to implantation into the body, with both proximal end 132 of tubular strut 138 and distal end 134 of tubular strut 138 being closed once the drug is loaded within central lumen 348. By "pre-loaded" it is meant that the therapeutic substance or drug may be filled, injected, or otherwise provided within central lumen 348 of tubular strut 138. Once loaded, both the proximal end 132 and the distal end 134 of tubular strut 138 are sealed or plugged prior to delivery into the body. Proximal end 132 and distal end 134 may be sealed with a plug (not shown), such as a plug of silicone. As previously described, the therapeutic substance may be suspended in an optionally biodegradable polymer matrix or carrier to prevent premature elution of the active therapeutic substance from central lumen 348 until stent 130 has been deployed at the treatment site. Once positioned inside of the body at the desired location, stent 130 is deployed for permanent implantation in the body lumen such that the therapeutic substance may elute from channel 136.

In addition, a readily dissolvable coating (not shown) may be utilized in embodiments of the present invention in order to prevent premature elution of the active therapeutic substance from central lumen 348 until stent 130 has been deployed at the treatment site. The coating may fill or close up channel 136, or may cover the outside surface of tubular strut 138, or both. The coating may be a dextran type or any other appropriate coating that would dissolve very quickly, yet protect the therapeutic substance or drug as it is being delivered to the stenotic site. For example, coating materials that are sufficient to provide the desired short duration protection, such as polysaccharides including mannitol, sorbitol, sucrose, xylitol, anionic hydrated polysaccharides such as gellan, curdlan, XM-6, xanthan, are listed in U.S. Pat. No. 6,391,033, which is incorporated by reference herein in its entirety. These materials dissolve in approximately ten to fifteen minutes in order to allow for proper stent placement at the target site.

In various embodiments of the present invention, tubular strut 138 may be made from a metallic material. For example, tubular strut 138 may be manufactured from any suitable metallic materials including stainless steel, nickel-titanium (nitinol), nickel-cobalt alloy such as MP35N, cobalt-chromium, tantalum, titanium, platinum, gold, silver, palladium, iridium, and the like. In an alternate embodiment, tubular strut 138 may be made from a hypotube. As is known in the art, a hypotube is a hollow metal tube of very small diameter, of the type typically used in manufacturing hypodermic needles. If tubular strut 138 is manufactured of nickel-titanium (nitinol), deployment of stent 130 may be facilitated by utilizing the shape memory of the material, as explained below. Once implanted, the metallic stent provides artificial radial support to the wall tissue.

Embodiments of the present invention also include tubular strut 138 being formed from a non-metallic material, such as a polymeric material. The polymeric material may be biodegradable or bioresorbable such that stent 130 is absorbed in the body after being utilized to restore patency to the lumen and/or provide drug delivery. As previously mentioned, spiral or corkscrew channel 136 includes width 240, which may be selected in order to control the elution rate of the therapeutic substance or drug. In general, a wider diameter "D" of channel 136 will reduce the remaining material of stent 130 and thus may be desirable if stent 130 is formed of a biodegradable material.

In the embodiment of FIG. 1, stent 130 is balloon-expandable, such that when a source of inflation fluid is connected to inflation port 118 of hub 116 balloon 110 may be inflated to expand stent 130 as is known to one of ordinary skill in the art. If desired, a sheath (not shown) may be provided to surround stent 130 on balloon 110 to facilitate tracking of the stent delivery system 100 over guidewire 128 through the vasculature to a site of a stenotic lesion.

In another embodiment, stent 130 may be self-expanding. Deployment of stent 130 may be facilitated by utilizing shape memory characteristics of a material such as nickel-titanium (nitinol). More particularly, shape memory metals are a group of metallic compositions that have the ability to return to a defined shape or size when subjected to certain thermal or stress conditions. Shape memory metals are generally capable of being deformed at a relatively low temperature and, upon exposure to a relatively higher temperature, return to the defined shape or size they held prior to the deformation. This enables the stent to be inserted into the body in a deformed, smaller state so that it assumes its "remembered" larger shape once it is exposed to a higher temperature, i.e., body temperature or heated fluid, in vivo. Thus, self-expanding stent 130 can have two states of size or shape, a contracted or compressed configuration sufficient for delivery to the treatment site and a deployed or expanded configuration having a generally cylindrical shape for contacting the vessel wall.

In another embodiment in which stent 130 is self-expanding, stent 130 may be constructed out of a spring-type or superelastic material such as nickel-titanium (nitinol), a nickel-tin alloy, a shape memory material, and other superelastic materials. A sheath (not shown) may be provided to surround and contain stent 130 in a contracted or compressed position. Once stent 130 is in position at a site of a stenotic lesion, the sheath may be retracted, thus releasing stent 130 to assume its expanded or deployed configuration.

Figure 6:
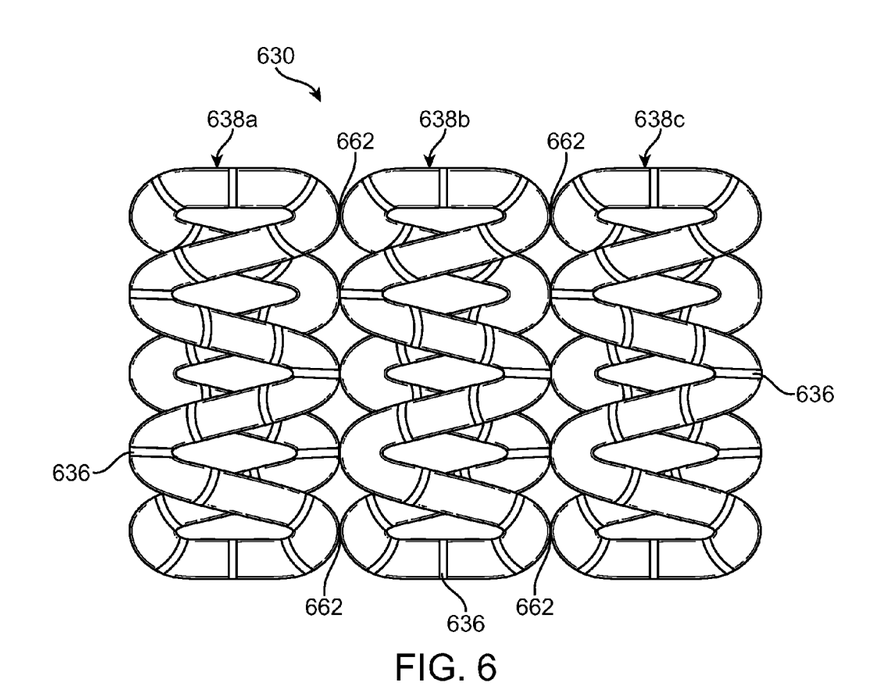
FIG. 6 is a side view of a stent in accordance with another embodiment of the present invention.

As previously stated, stent 130 is formed from a tubular strut 138. In FIGS. 1, 4, and 5, tubular strut 138 is shaped into a helical or coiled configuration to form substantially cylindrical stent 130. FIG. 6 shows an alternate stent configuration in which multiple tubular struts 638a, 638b, and 638c are bonded together at joints 662. Each tubular strut 638a, 638b, 638c is the same as tubular strut 138, in that each includes a continuous channel 636 positioned spirally about or in a corkscrew fashion around a circumference of tubular strut 638a, 638b, and 638c for delivering a therapeutic substance or drug. Each tubular strut 638a, 638b, 638c is formed into an undulating or zigzag ring configuration, and are bonded together at joints 662 to form stent 630. Although FIG. 6 illustrates three tubular struts 638a, 638b, 638c bonded together to form stent 630, as few as one tubular strut in an undulating or zigzag ring configuration may form stent 630. In addition, stent 630 may include numerous tubular struts having an undulating or zigzag ring configuration bonded together.

Each tubular strut 638a, 638b, 638c may contain the same or a different therapeutic substance or drug for delivery. Further, each tubular strut 638a, 638b, 638c may contain a different concentration of therapeutic substance or drug for delivery. For example, tubular struts 638a and 638c located at the ends of stent 630 may contain a first concentration of a therapeutic substance or drug, and tubular strut 638b located intermediate the ends of stent 630 may contain a second concentration of a therapeutic substance or drug. The second concentration of the therapeutic substance or drug may be higher or lower than the first concentration of the therapeutic substance or drug.

Figure 7:
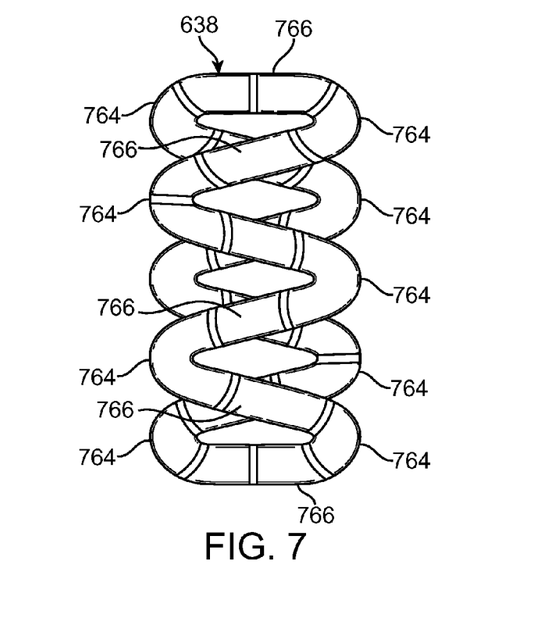
FIG. 7 is a side view of a single tubular strut of the stent in FIG. 6.
Figure 7A:
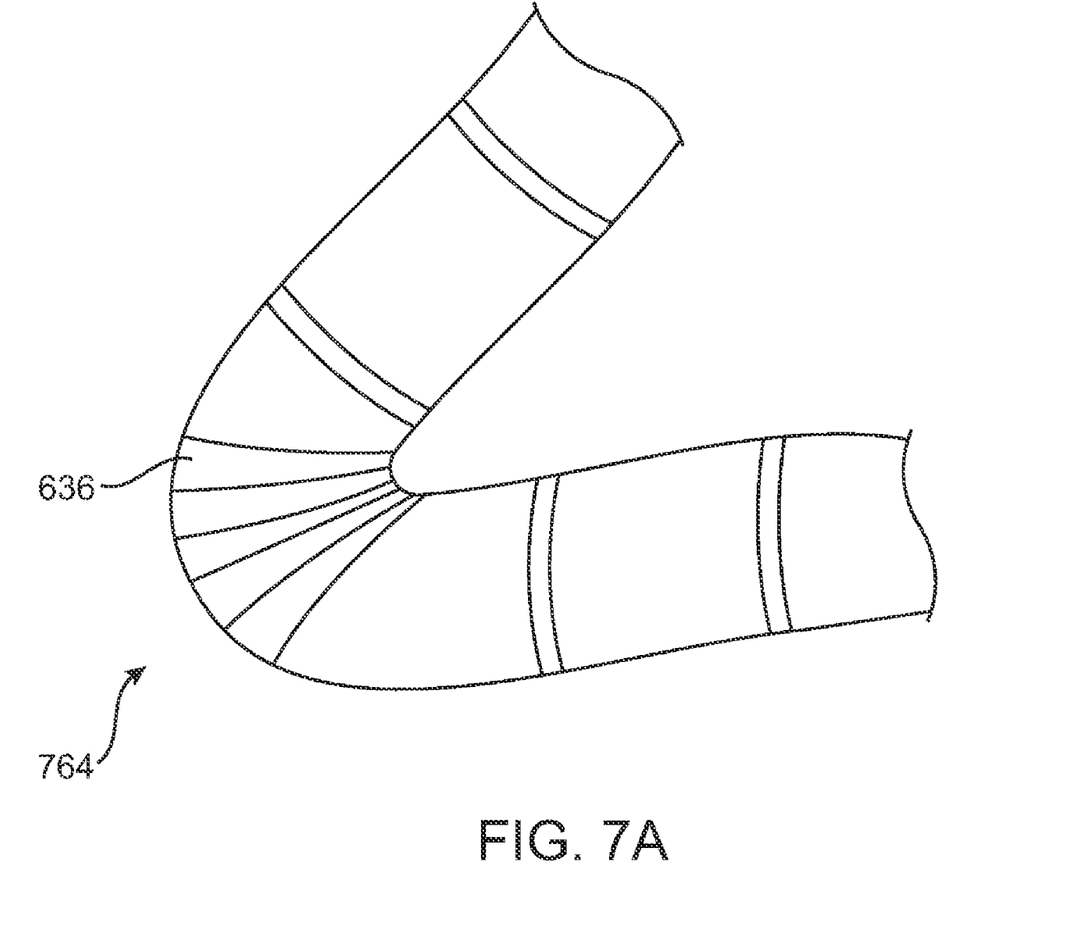
FIG. 7A is an enlarged view of a portion of the single tubular strut in FIG. 7.

FIG. 7 illustrates a single tubular strut 638 in an undulating or zigzag ring configuration. As shown in FIG. 7, the undulating or zigzag ring configuration includes crowns or turns 764 connected to straight segments 766. Crowns 764 are alternating turns facing opposite longitudinal directions. As described with reference to the previous embodiment, both the pitch and width of spiral or corkscrew channel 636 may be varied along the length of tubular strut 638. For example, the pitch of spiral or corkscrew channel 636 may be decreased at a particular location on tubular strut 638 in order to increase flexibility of stent 630 at that particular location. Further, the width of spiral or corkscrew channel 636 may be increased at a particular location on tubular strut 638 in order to increase flexibility of stent 630 at that particular location. As illustrated in FIG. 7A, decreased pitch and increased width of channel 636 may be desirable at crowns 764 when tubular strut 638 is formed into an undulating or zigzag ring configuration.

It is to be understood that tubular strut 138 may be shaped into any generally cylindrical configuration to form a stent body. In addition to the stent configurations shown above, FIG. 5 of U.S. Pat. No. 5,891,108, previously incorporated by reference, illustrates a stent in an alternate suitable stent configuration. Further, a tubular strut according to embodiments of the present invention may be formed into the stent configurations disclosed in U.S. Pat. No. 5,133,732 and U.S. Pat. No. 6,663,661, which are incorporated by reference herein in their entirety.

Stent 130 is manufactured from tubular strut 138. The stent would be manufactured by filling a hollowed wire or hypotube with a removable material. The removable material would act to stiffen the wire against buckling during the bending process. During the bending process, tubular strut 138 may be shaped into any generally cylindrical configuration described above to form the stent body. The bending process would be similar to the process used to form the design of the Medtronic Wiktor stent, which is disclosed in U.S. Pat. Nos. 4,886,062; 4,969,458; 5,133,732; 5,653,727; 5,782,903; 6,113,621; 6,656,219; and 6,923,828, which are incorporated by reference herein in their entirety. If the stent is constructed of nitinol, the formed stent would be thermally set. In addition, the formed stent may be welded if additional axial strength is required.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A drug eluting stent having a generally cylindrical configuration for placement within a body lumen, the stent comprising:
    a strut formed from a hollow wire or tube having a central lumen defined by an inner surface of the hollow wire or tube, wherein the strut is coiled to form the generally cylindrical configuration of the stent;
    an open channel formed in a spiraling fashion to wrap around a circumference of the strut along a length of the strut that extends from substantially a proximal end to a distal end thereof, the spiral channel having a depth that extends between an outer surface of the hollow wire or tube that forms the strut to the central lumen thereof; and
    a therapeutic substance disposed within the central lumen of the strut for delivery to a body vessel via the spiral channel to provide distribution of the therapeutic substance to the body vessel's luminal and abluminal surfaces.

2. The drug delivery apparatus of claim 1, wherein the spiral channel has a width that is varied along a length of the strut such that the width of the spiral channel is greater at a first location of the stent than at a second location of the stent.

3. The drug delivery apparatus of claim 2, wherein the spiral channel is formed by a laser and the width is varied by controlling the laser focus.

4. The drug delivery apparatus of claim 2, wherein the first location is a turn of the strut in the generally cylindrical configuration of the stent.

5. The drug delivery apparatus of claim 1, wherein the spiral channel has a pitch that is varied along a length of the strut such that the pitch of the spiral channel is smaller at a first location of the stent than at a second location of the stent.

6. The drug delivery apparatus of claim 5, wherein the first location is a turn of the strut in the generally cylindrical configuration of the stent.

7. The drug delivery apparatus of claim 1, wherein the strut is made of a metallic material.

8. The drug delivery apparatus of claim 1, wherein the strut is made of a tube of a biodegradable polymer.

9. The drug delivery apparatus of claim 1, wherein the therapeutic substance is in crystalline form.

10. The drug delivery apparatus of claim 1, wherein the therapeutic substance is contained in a polymer matrix to control elution.

11. The drug delivery apparatus of claim 10, wherein the polymer matrix is biodegradable.

12. A drug eluting stent having a generally cylindrical configuration for placement within a body lumen, the stent comprising:
    a tubular strut having a central lumen defined by an inner surface of the tubular strut, the tubular strut shaped into an undulating or zigzag ring that forms the generally cylindrical configuration of the stent;
    an open channel formed in a spiraling fashion to wrap around a circumference of the tubular strut along a length of the tubular strut that extends from substantially a proximal end to a distal end thereof, the spiral channel having a depth that extends between an outer surface and the central lumen of the tubular strut; and
    a therapeutic substance disposed within the central lumen of the tubular strut for delivery to a body vessel via the spiral channel to provide distribution of the therapeutic substance to the body vessel's luminal and abluminal surfaces.

13. A drug eluting stent having a generally cylindrical configuration for placement within a body lumen, the stent comprising:
    a strut formed from a tube that defines a central lumen, the tubular strut shaped into the generally cylindrical configuration of the stent;
    an open channel formed in a spiraling fashion to wrap around a circumference of the tubular strut along a length of the tubular strut that extends from substantially a proximal end to a distal end thereof, the spiral channel having a depth that extends between an outer surface and the central lumen of the tube that forms the strut, wherein a pitch of the spiral channel is varied along the tubular strut length; and
    a therapeutic substance disposed within the central lumen of the tubular strut for delivery to a body vessel via the spiral channel to provide distribution of the therapeutic substance to the body vessel's luminal and abluminal surfaces.

14. The drug delivery apparatus of claim 13, wherein the spiral channel has a width that is varied along the length of the tubular strut such that the width of the spiral channel is greater at a first location of the stent than at a second location of the stent.

15. The drug delivery apparatus of claim 14, wherein the spiral channel is formed by a laser and the width is varied by controlling the laser focus.

16. The drug delivery apparatus of claim 14, wherein the first location is a turn of the generally cylindrical configuration of the stent.

17. The drug delivery apparatus of claim 13, wherein the pitch of the spiral channel is smaller at a first location of the stent than at a second location of the stent.

18. The drug delivery apparatus of claim 17, wherein the first location is a turn of the generally cylindrical configuration of the stent.

19. The drug delivery apparatus of claim 13, wherein the tubular strut is made of a metallic material.

20. The drug delivery apparatus of claim 13, wherein the tubular strut is made of a biodegradable polymer.

21. The drug delivery apparatus of claim 13, wherein the therapeutic substance is in crystalline form.

22. The drug delivery apparatus of claim 13, wherein the therapeutic substance is contained in a polymer matrix to control elution.

23. The drug delivery apparatus of claim 22, wherein the polymer matrix is biodegradable.

* * * * *